United States Patent
Wollrab et al.

(10) Patent No.: US 8,907,143 B2
(45) Date of Patent: Dec. 9, 2014

(54) PROCESS FOR PRODUCING ETHANOL BY HYDROGENATING MIXED FEEDS COMPRISING WATER

(75) Inventors: Radmila Wollrab, Pasadena, TX (US); Zhenhua Zhou, Houston, TX (US); Victor J. Johnston, Houston, TX (US); David Lee, Seabrook, TX (US); R. Jay Warner, Houston, TX (US); Heiko Weiner, Pasadena, TX (US)

(73) Assignee: Celanese International Corporation, Irving, TX (US)

( * ) Notice: Subject to any disclaimer, the term of this patent is extended or adjusted under 35 U.S.C. 154(b) by 229 days.

(21) Appl. No.: 13/543,144

(22) Filed: Jul. 6, 2012

(65) Prior Publication Data

US 2013/0158300 A1 Jun. 20, 2013

Related U.S. Application Data

(60) Provisional application No. 61/576,052, filed on Dec. 15, 2011.

(51) Int. Cl.
*C07C 29/12* (2006.01)

(52) U.S. Cl.
USPC ............ 568/890; 568/881; 568/884; 568/885

(58) Field of Classification Search
None
See application file for complete search history.

(56) References Cited

U.S. PATENT DOCUMENTS

| | | | | |
|---|---|---|---|---|
| 6,768,021 B2 * | 7/2004 | Horan et al. | ............ | 560/265 |
| 6,809,217 B1 * | 10/2004 | Colley et al. | ............ | 560/231 |
| 2003/0135069 A1 | 7/2003 | Fujita et al. | | |
| 2003/0191020 A1 | 10/2003 | Bharadwaj et al. | | |
| 2004/0195084 A1 | 10/2004 | Hetherington et al. | | |
| 2004/0242917 A1 | 12/2004 | Inui et al. | | |
| 2005/0028435 A1 | 2/2005 | Pace et al. | | |
| 2005/0181940 A1 | 8/2005 | Wang et al. | | |
| 2006/0106246 A1 | 5/2006 | Warner et al. | | |
| 2009/0166172 A1 | 7/2009 | Casey et al. | | |
| 2009/0209786 A1 | 8/2009 | Scates et al. | | |
| 2009/0259086 A1 | 10/2009 | Bailey et al. | | |
| 2009/0326268 A1 | 12/2009 | Hanes et al. | | |
| 2011/0224462 A1 | 9/2011 | Ditzel et al. | | |

FOREIGN PATENT DOCUMENTS

| | | |
|---|---|---|
| EP | 0137749 | 4/1985 |
| EP | 0175558 | 3/1986 |
| EP | 0407038 | 1/1991 |
| EP | 2060553 | 5/2009 |
| WO | WO 2008/135192 | 11/2008 |

OTHER PUBLICATIONS

Sarsfield, "Powder x-ray diffraction detection of crystalline phases in amorphous pharamceuticals," Advances in x-ray analysis, International Centre for Diffraction Data, US v. 49, Jan. 1, 2006, pp. 322-327.

Nefedov and I V Mishin B K, "Synthesis of diethyl ether in presence of zeolite catalysts", Russian Chem. Bull., Springer Anew York LLC, v. 28, Jan. 1, 1979, pp. 183-186.

* cited by examiner

*Primary Examiner* — Sudhakar Katakam

(57) ABSTRACT

The processes of the current invention relate to the production of ethanol from a crude ethanol product obtained from the hydrogenation of acetic acid and ethyl acetate. Conversion of ethyl acetate may be improved by controlling the water content that may be fed to the vaporizer to form a feed stream that may be fed to the hydrogenation reactor. At least 0.01 wt. % water is fed to the vaporizer. The crude ethanol product is separated two or more columns to yield an ethanol product.

17 Claims, 3 Drawing Sheets

PROCESS FOR PRODUCING ETHANOL BY HYDROGENATING MIXED FEEDS COMPRISING WATER

CROSS REFERENCE TO RELATED APPLICATION

This application claims priority to U.S. Prov. App. No. 61/576,052, filed on Dec. 15, 2011, the entire contents and disclosures of which are incorporated herein by reference.

FIELD OF THE INVENTION

The present invention relates generally to processes for recovering ethanol produced by the hydrogenation of acetic acid, ethyl acetate, and mixtures thereof. In particular, the present invention relates to feeding at least 0.01 wt. % water to the vaporizer to form a feed stream that may be fed to the hydrogenation reactor to yield improved ethyl acetate conversion.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulosic materials, such as corn or sugar cane. Conventional methods for producing ethanol from organic feed stocks, as well as from cellulosic materials, include the acid-catalyzed hydration of ethylene, methanol homologation, direct alcohol synthesis, and Fischer-Tropsch synthesis. Instability in organic feed stock prices contributes to fluctuations in the cost of conventionally produced ethanol, making the need for alternative sources of ethanol production all the greater when feed stock prices rise. Starchy materials, as well as cellulosic materials, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol product and a stream of acetic acid and ethyl acetate, which is recycled to the hydrogenation reactor.

U.S. Pat. No. 7,842,844 describes a process for improving selectivity and catalyst activity and operating life for the conversion of hydrocarbons to ethanol and optionally acetic acid in the presence of a particulate catalyst, said conversion proceeding via a syngas generation intermediate step.

US Pub. No. 2011/0224462 a process for producing methanol and ethanol, wherein the methanol is produced from synthesis gas and the ethanol is produced via the hydrogenation of an ethanoic acid feed. The hydrogenation of the ethanoic acid feed is carried out within the same alcohol synthesis unit and in the presence of the same catalyst(s) that is used to produce the methanol from the synthesis gas and wherein the feed introduced to the alcohol synthesis unit comprises synthesis gas and ethanoic acid. The ethanoic acid feed may contain water in an amount between 0.5 and 20 mol %.

The need remains for improved processes for recovering ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol, comprising: hydrogenating a feed stream in a reactor in the presence of a catalyst to form a crude ethanol product; and separating at least a portion of the crude ethanol product in two or more columns to produce ethanol and a liquid recycle stream comprising ethyl acetate, ethanol, water and/or acetaldehyde or mixtures thereof. The feed stream is produced by vaporizing an acetic acid stream, the liquid recycle stream and a water stream in a vaporizer; and wherein the total amount of water fed to the vaporizer is at least 0.01 wt. %, e.g., at least 0.1 wt. % or at least 1 wt. %. In terms of ranges, the feed stream fed to the vaporizer comprises from 0.01 wt. % to 20 wt. % water, e.g., from 0.1 wt. % to 15 wt. % water. The volumetric ratio of acetic acid stream to liquid recycle stream is at least 1.5:1 and may range from 1.5:1 to 20:1, e.g., from 1.5:1 to 5:1. In one embodiment, the conversion of ethyl acetate is at least 0.01%, e.g., at least 0.1% or at least 8%. The catalyst preferably is substantially free of copper, zinc, and oxides thereof. In one embodiment, the catalyst comprises a first metal selected from the group consisting of iron, cobalt, nickel, ruthenium, rhodium, palladium, osmium, iridium, platinum, titanium, chromium, rhenium, molybdenum, and tungsten, and a second metal is selected from the group consisting of molybdenum, tin, chromium, iron, cobalt, vanadium, tungsten, palladium, platinum, lanthanum, cerium, manganese, ruthenium, rhenium, gold, and nickel, wherein the second metal is different than the first metal.

In a second embodiment, the present invention is directed to a process for producing ethanol, comprising: hydrogenating a feed stream in a reactor in the presence of a catalyst to form a crude ethanol product; separating at least a portion of the crude ethanol product in a first distillation column to yield a first residue comprising acetic acid and a first distillate comprising ethanol, ethyl acetate, and water; removing water from at least a portion of the first distillate to yield an ethanol mixture stream comprising less than 10 wt. % water; and separating a portion of the ethanol mixture stream in a second distillation column to yield a second residue comprising ethanol and a second distillate comprising ethyl acetate; wherein the feed stream is produced by vaporizing an acetic acid stream, the second distillate and a water stream in a vaporizer; and wherein the total amount of water fed to the vaporizer is at least 0.01 wt. %.

In a third embodiment, the present invention is directed to a process for producing ethanol, comprising: hydrogenating a feed stream in a reactor in the presence of a catalyst to form a crude ethanol product; separating a portion of the crude ethanol product in a first distillation column to yield a first distillate comprising ethyl acetate and acetaldehyde, and a first residue comprising ethanol, acetic acid, water or mixtures thereof; separating a portion of the first residue in a second distillation column to yield a second residue comprising acetic acid and water and a second distillate comprising ethanol and ethyl acetate; and separating a portion of the second distillate in a third distillation column to yield a third residue comprising ethanol and a third distillate comprising ethyl acetate; wherein the feed stream is produced by vaporizing an acetic acid stream, the third distillate and a water stream in a vaporizer; and wherein the total amount of water fed to the vaporizer is at least 0.01 wt. % water, e.g., from 0.01 to 20 wt. %. An extractive agent may be fed to the first column. At least a portion of the second residue may be used as the extractive agent. The catalyst may be substantially free of copper, zinc and oxides thereof.

In a fourth embodiment, the present invention is directed to a process for producing ethanol, comprising: hydrogenating a feed stream in a reactor in the presence of a catalyst to form a crude ethanol product; and separating at least a portion of the crude ethanol product in two or more columns to produce ethanol and a liquid recycle stream; wherein the feed stream is produced by vaporizing an acetic acid stream, the liquid recycle stream and a water stream; and wherein more water is fed to the vaporizer than ethanol on a molar basis. A volumetric ratio of acetic acid stream to liquid recycle stream may be at least 1.5:1.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1:
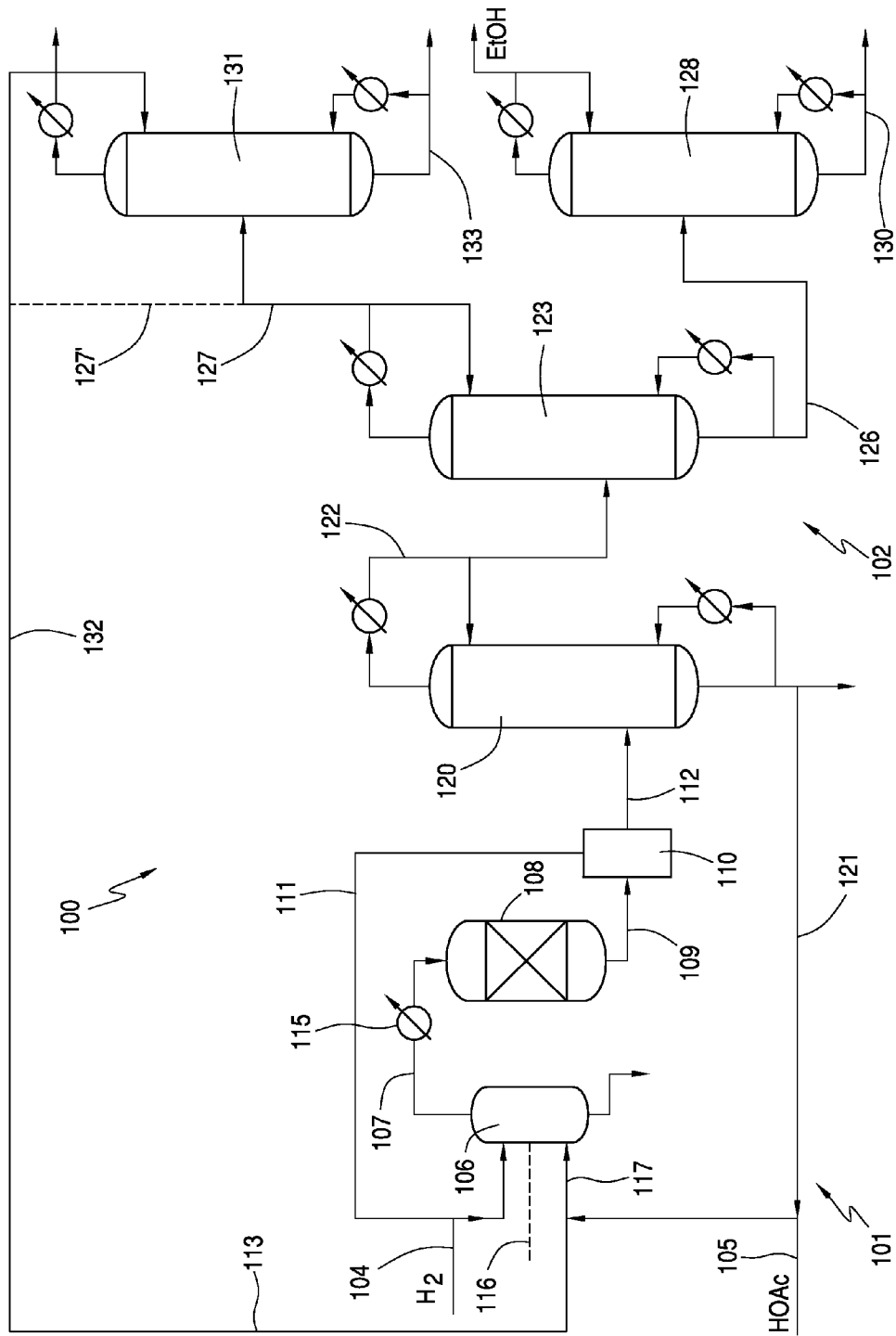
FIG. 1 is a schematic diagram of a hydrogenation process in accordance with an embodiment of the present invention.

The present invention relates to processes for producing ethanol by vaporizing acetic acid and ethyl acetate in a vaporizer to form a feed stream and hydrogenating the feed stream in a reactor in the presence of a catalyst. A crude ethanol product that comprises ethanol, water, ethyl acetate, acetaldehyde, acetic acid, and other impurities is withdrawn from the hydrogenation reactor. For purposes of the present invention the hydrogenation reactor does not produce any methanol, or methanol derivatives such as methyl acetate or dimethyl ether. The processes of the present invention further comprise separating the crude ethanol product to recover ethanol. In some embodiments, at least two distillation columns are used to separate the crude product. Distillate streams comprising ethyl acetate and acetaldehyde may be recycled to the vaporizer as liquid recycle streams to reduce the amount of purges. The liquid recycle stream preferably comprises ethyl acetate and is substantially free of acetic acid. The liquid recycle stream may also comprise mixtures of acetaldehyde, diethyl acetal, ethanol and/or water. The liquid recycle stream is combined with a fresh acetic acid stream, i.e. an acetic acid stream that has not been passed over a catalyst, and both the liquid recycle stream and acetic acid reactants are vaporized in the presence of hydrogen to yield a feed stream comprising vapor phase reactants.

In one embodiment, water is fed to the vaporizer. Water may be fed separately to the vaporizer as a water stream or may be combined with the acetic acid stream and liquid recycle streams and then fed to the vaporizer. Preferably water is from a liquid recycle stream obtained by separating the crude ethanol product and is fed to the vaporizer. The present of water in the liquid recycle stream does not substantially impact the reactor and may improve the performance of the catalyst, in particular for mixtures of acetic acid and ethyl acetate. This may reduce the energy required to purify the recycle streams because it is not necessary to completely dry the recycle stream before returning them to the reactor. The liquid recycle stream may comprise acetic acid, ethyl acetate, acetaldehyde, or mixtures thereof. Water may also be fed to the vaporizer from an external source, such as contained in the acetic acid feed source as described in US Pub. Nos. 2012/0059197 or 2012/0010439, the entire contents and disclosures of which are hereby incorporated by reference. The total amount of water that may be fed to the vaporizer is at least 0.01 wt. %, e.g., at least 0.1 wt. % or at least 1 wt. %. In terms of ranges, the total amount of water that may be fed to the vaporizer is from 0.01 wt. % to 20 wt. %, e.g., from 0.1 wt. % to 15 wt. % or from 1 wt. % to 15 wt. %. In some embodiments, more water is fed to the vaporizer than ethanol, on a molar basis.

In some embodiments, acetic acid stream and/or the liquid recycle stream may comprise water. Thus, no separate water stream may be needed when the acetic acid stream and/or liquid recycle stream comprise water.

When the liquid recycle stream, acetic acid stream and water stream are fed to the vaporizer to yield a feed stream, the total amount of water fed to the vaporizer is at least 0.01 wt. %. The feed stream from the vaporizer is then fed to the reactor. Due to the presence of both ethyl acetate and acetic acid in the feed stream, the catalyst in the reactor preferably converts both ethyl acetate and acetic acid. Generally, the conversion of acetic acid is relatively larger than ethyl acetate. Also ethyl acetate conversions may be negative, which may lead to a net production of ethyl acetate rather than consuming ethyl acetate in the reactor. To maintain sufficient conversion of ethyl acetate, the present invention feeds water to the vaporizer.

It has surprisingly and unexpectedly been found that when at least 0.01 wt. % water is fed to the vaporizer, the conversion of ethyl acetate in the reactor may be improved. The conversion of ethyl acetate is at least 1%, e.g., at least 3% or at least 15%. For example, some of the water may hydrolyze the ethyl acetate, thereby reducing the ethyl acetate concentration in the reactor. Thus, there is an additional hydrolysis reaction, in the vapor phase, occurring in the same reactor as the hydrogenation of acetic acid. In some embodiments, ethyl acetate conversions may be increased by increasing the water fed to the vaporizer. In addition, feeding additional water does not significantly impact the acetic acid conversion.

In one embodiment, the volumetric ratio of acetic acid stream to liquid recycle stream may be at least 1.5:1, e.g., at least 2:1 or at least 5:1. In terms of ranges, the volumetric ratio of acetic acid stream to liquid recycle stream may be from 1.5:1 to 20:1, e.g., from 1.5:1 to 5:1. Generally, the molar ratio of acetic acid to ethyl acetate in the vaporizer is greater than 1:1, e.g., greater than 1.5:1 or greater than 2:1. The vaporizer may be operate at a temperature from 20° C. to 300° C. and may operate at a pressure from 10 kPa to 3000 kPa. In some embodiments, under the conditions in the vaporizer, a non-catalyzed reaction may occur to drive the formation of additional ethyl acetate and reduce the amount of fresh acetic acid. Without being bound by theory the presence of water in the feed water may also suppress the formation of ethyl acetate. In addition, because the vapor feed stream may be further heated prior to the reactor, additional undesired esterification of the fresh acetic acid in the feed stream may occur. Generally, the vapor feed stream exits the vaporizer at a temperature of about 120° C. and is further heated to a temperature of about 275° C. before entering the reactor. Typically, lowering the temperature of the vapor stream feed would reduce the formation of additional ethyl acetate. However, because of the pre-heating step required in the present processes, the formation of ethyl acetate cannot be controlled by cooling the vapor stream feed and thus more ethyl acetate is fed to the reactor.

In recovering ethanol, the processes of the present invention may use two or more distillation columns. In one embodiment, a first distillation column is used to separate the feed stream into a residue stream comprising acetic acid. Depending on where the ethanol is concentration, either in the distillate or residue, the stream containing the ethanol from the first distillation column may be subsequently separated to obtain ethanol. The remaining streams may be returned to the vaporizer as the liquid recycle streams. There may be at least one liquid recycle stream that comprises ethyl acetate from this separation.

In another embodiment, a first distillation column is used to separate the feed stream into a residue stream comprising water and acetic acid from the crude ethanol product and a distillate stream comprising ethanol, acetaldehyde and ethyl acetate. The residue may comprise a substantial portion of the water. In one embodiment, 30 to 90% of the water in the crude ethanol product is removed in the residue, e.g., from 40 to 88% of the water or from 50 to 84% of the water. Water may also be removed from the distillate to form an ethanol mixture stream, preferably comprising less than 10 wt. % water, less than 6 wt. % water or less than 4 wt. % water. In terms of ranges the ethanol mixture stream comprises from 0.001 to 10 wt. % water, e.g., from 0.01 to 6 wt. % water or from 0.1 to 4 wt. % water. Water may be removed, for example, using an adsorption unit, membrane, molecular sieves, extractive column distillation, or a combination thereof. Suitable adsorption units include pressure swing adsorption (PSA) units and thermal swing adsorption (TSA) units. The adsorption units may comprise molecular sieves, such as aluminosilicate compounds. Product ethanol is then recovered from the ethanol mixture stream. There may be at least one liquid recycle stream that comprises ethyl acetate that is also recovered from the ethanol mixture stream.

In another embodiment, a first distillation column is used to separate the crude stream into a residue stream comprising ethanol, ethyl acetate, water and acetic acid and a distillate stream comprising acetaldehyde and ethyl acetate. The distillate may be the liquid recycle stream. The residue stream, for example, may comprise at least 50% of the ethanol from the crude ethanol product, and more preferably at least 70%. In terms of ranges, the residue stream may comprise from 50% to 99.9% of the ethanol from the crude ethanol product, and more preferably from 70% to 99%. Preferably, the amount of ethanol from the crude ethanol recovered in the residue may be greater than 97.5%, e.g. greater than 99.9%.

The residue may also comprise a substantial portion of the water and acetic acid from the crude ethanol product. The residue stream comprising ethanol, ethyl acetate, water, and acetic acid may be further separated to recover ethanol. Because these compounds may not be in equilibrium, additional ethyl acetate may be produced through esterification of ethanol and acetic acid. In one preferred embodiment, the water and acetic acid may be removed as another residue stream in a separate distillation column. In addition, the water carried over in the separate distillation column may be removed with a water separator that is selected from the group consisting of an adsorption unit, membrane, extractive column distillation, molecular sieves, and combinations thereof.

Although ethyl acetate is partially withdrawn into the first distillate, a higher ethyl acetate concentration in the first residue leads to increased ethanol concentration in the first residue and decreased ethanol concentrations in the first distillate. Thus, overall ethanol recovery may be increased. Depending on the ethyl acetate concentration in the residue and whether there is in situ esterification in the residue or an esterification reactor, it may be necessary to further separate the ethyl acetate and ethanol in a separate column. Preferably, this separate column is located after the water has been removed using a distillation column and/or water separator. Generally, a separate column may be necessary when the residue comprises at least 50 wppm ethyl acetate or there is in situ esterification. When the ethyl acetate is less than 50 wppm, it may not be necessary to use separate column to separate ethyl acetate and ethanol.

Ethyl acetate may be separated from ethanol in a separate column near the end of the purification process. In removing ethyl acetate, additional light organics may also be removed, thus improving the quality of the ethanol product by decreasing impurities. Preferably, water and/or acetic acid may be removed prior to the ethyl acetate/ethanol separation. In one embodiment, after the ethyl acetate is separated from ethanol, the ethyl acetate is returned to the initial column and fed near the top of that column. This allows for any ethanol removed with the ethyl acetate to be recovered and further reduces the amount of ethanol being recycled to the reactor. In some embodiments, it is preferably to recycle ethanol within the separation zone but to decrease the amount of ethanol recycled to the reactor. Decreasing the amount of ethanol recycled to the reactor may reduce reactor capital and improve efficiency in recovering ethanol. Preferably, the ethyl acetate is removed in the distillate of the first column and returned to the reactor with the acetaldehyde.

In preferred embodiments, the residue stream of the first column comprises a substantial portion of the water and the acetic acid from the crude ethanol stream. The residue stream may comprise at least 80% of the water from the crude ethanol stream, and more preferably at least 90%. In terms of ranges, the residue stream preferably comprises from 80% to 100% of the water from the crude ethanol stream, and more preferably from 90% to 99.4%. The residue stream may comprise at least 85% of the acetic acid from the crude ethanol stream, e.g., at least 90% and more preferably about 100%. In terms of ranges, the residue stream preferably comprises from 85% to 100% of the acetic acid from the crude ethanol stream, and more preferably from 90% to 100%. In one embodiment, substantially all of the acetic acid is recovered in the residue stream.

In one embodiment, each of the columns is sized to be capital and economically feasible for the rate of ethanol production. The total diameter for the columns used to separate the crude ethanol stream may be from 5 to 40 meters, e.g., from 10 to 30 meters or from 12 to 20 meters. Each column may have a varying size. In one embodiment, the ratio of column diameter in meters for all the distillation columns to tons of ethanol produced per hour is from 1:2 to 1:30, e.g., from 1:3 to 1:20 or from 1:4 to 1:10. This would allow the process to achieve production rates of 25 to 250 tons of ethanol per hour.

The distillate from the initial column comprises light organics, such as acetaldehyde, diethyl acetal, acetone and ethyl acetate. In addition, minor amounts of ethanol and water may be present in the distillate. Removing these light organic components from the crude ethanol stream in the initial column provides an efficient means for removing acetaldehyde and ethyl acetate. In addition, acetaldehyde, diethyl acetal and acetone are not carried over with the ethanol when multiple columns are used, thus reducing the formation of byproducts from acetaldehyde, diethyl acetal, and acetone. In particular, acetaldehyde and/or ethyl acetate may be returned to the reactor, and converted to additional ethanol. In another embodiment, a purge may remove these light organics from the system.

The residue from the initial column comprises ethyl acetate. Although ethyl acetate is also partially withdrawn into the first distillate, a higher ethyl acetate concentration in the first residue leads to increased ethanol concentration in the first residue and decrease ethanol concentrations in the first distillate. Thus overall ethanol recovery may be increased. Ethyl acetate may be separated from ethanol in a separate column near the end of the purification process. In removing ethyl acetate, additional light organics may also be removed and thus improve the quality of the ethanol product by decreasing impurities. Preferably, water and/or acetic acid may be removed prior to the ethyl acetate/ethanol separation.

In one embodiment, after the ethyl acetate is separated from ethanol, the ethyl acetate is returned to the initial column and fed near the top of that column. This allows for any ethanol removed with the ethyl acetate to be recovered and further reduces the amount of ethanol being recycled to the reactor. Decreasing the amount of ethanol recycled to the reactor may reduce reactor capital and improve efficiency in recovering ethanol. Preferably, the ethyl acetate is removed in the distillate of the first column and returned to the reactor with the acetaldehyde.

Hydrogenation of Acetic Acid

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, fed to the reactor used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Biomass-derived syngas has a detectable $^{14}C$ isotope content as compared to fossil fuels such as coal or natural gas. An equilibrium forms in the Earth's atmosphere between constant new formation and constant degradation, and so the proportion of the $^{14}C$ nuclei in the carbon in the atmosphere on Earth is constant over long periods. The same distribution ratio $n^{14}C:n^{12}C$ ratio is established in living organisms as is present in the surrounding atmosphere, which stops at death and $^{14}C$ decomposes at a half life of about 6000 years. Methanol, acetic acid and/or ethanol formed from biomass-derived syngas would be expected to have a $^{14}C$ content that is substantially similar to living organisms. For example, the $^{12}C$ ratio of the methanol, acetic acid and/or ethanol may be from one half to about 1 of the $^{12}C$ ratio for living organisms. In other embodiments, the syngas, methanol, acetic acid and/or ethanol described herein are derived wholly from fossil fuels, i.e. carbon sources produced over 60,000 years ago, may have no detectable $^{14}C$ content.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

Acetic acid fed to the hydrogenation reactor may also comprise other carboxylic acids and anhydrides, as well as aldehyde and/or ketones, such as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. In accordance with embodiments of the present invention, water may also be present in the acetic acid feed. Preferably, the feed to the hydrogenation reactor does not comprise syngas or a mixture of hydrogen, carbon monoxide, and/or carbon dioxide that would be similar to syngas. In other embodiments, the feed to the hydrogenation reactor does not contain alkanes including linear or cyclic alkane, such as ethane and/or cyclohexane.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The reactor pressure may range from 10 kPa to 3000 kPa, e.g., from 50 kPa to 2300 kPa, or from 100 kPa to 2100 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

The hydrogenation of acetic acid to form ethanol is preferably conducted in the presence of a hydrogenation catalyst in the reactor. The catalysts preferably are not methanol synthesis catalysts and are substantially free of copper and/or zinc, including oxides thereof. Suitable hydrogenation catalysts include catalysts comprising a first metal and optionally one or more of a second metal, a third metal or any number of additional metals, optionally on a catalyst support. Preferred bimetallic combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, nickel/palladium, gold/palladium, ruthenium/rhenium, and ruthenium/iron. Additional metal combinations may include palladium/rhenium/tin, palladium/rhenium/cobalt, palladium/rhenium/nickel, platinum/tin/palladium, platinum/tin/cobalt, platinum/tin/chromium, and platinum/tin/nickel.

The hydrogenation of acetic acid to form ethanol is preferably conducted in the presence of a hydrogenation catalyst. Exemplary catalysts are further described in U.S. Pat. Nos. 7,608,744 and 7,863,489, and U.S. Pub. Nos. 2010/0121114 and 2010/0197985, the entireties of which are incorporated herein by reference. In another embodiment, the catalyst comprises a Co/Mo/S catalyst of the type described in U.S. Pub. No. 2009/0069609, the entirety of which is incorporated herein by reference. In some embodiments the catalyst may be a bulk catalyst.

In one embodiment, the catalyst comprises a first metal selected from the group consisting of iron, cobalt, nickel, ruthenium, rhodium, palladium, osmium, iridium, platinum, titanium, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 7.5 wt. %. For catalysts comprising two or more metals, the two or more metals may be alloyed with one another or may comprise a non-alloyed metal solution or mixture.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, platinum, tin, and rhenium. More preferably, the third metal is selected from cobalt, palladium, and ruthenium. When present, the total weight of the third metal preferably is from 0.1 to 20 wt. %, e.g., from 0.1 to 10 wt. %, or from 0.1 to 7.5 wt. %. In one embodiment, the catalyst may comprise platinum, tin and cobalt.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 1 to 20 wt. %, or from 3 to 15 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica gel, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIIB metal oxides, (vi) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, and yttrium, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197985 referred to above, the entireties of which are incorporated herein by reference.

After the washing, drying and calcining of the catalyst is completed, the catalyst may be reduced in order to activate the catalyst. Reduction is carried out in the presence of a reducing gas, preferably hydrogen. The reducing gas is continuously passed over the catalyst at an initial ambient temperature that is increased up to 400° C. In one embodiment, the reduction is preferably carried out after the catalyst has been loaded into the reaction vessel where the hydrogenation will be carried out.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a percentage based on acetic acid in the feed. The conversion may be at least 40%, e.g., at least 50%, at least 60%, at least 70% or at least 80%. Although catalysts that have high conversions are desirable, such as at least 80% or at least 90%, in some embodiments a low conversion may be acceptable at high selectivity for ethanol.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethanol is at least 60%, e.g., at least 70%, or at least 80%. Preferred embodiments of the hydrogenation process also have low selectivity to undesirable products, such as methane, ethane, and carbon dioxide. The selectivity to these undesirable products preferably is less than 4%, e.g., less than 2% or less than 1%.

The term "productivity," as used herein, refers to the grams of a specified product, e.g., ethanol, formed during the hydrogenation based on the kilograms of catalyst used per hour. The productivity may range from 100 to 3,000 grams of ethanol per kilogram of catalyst per hour.

In various embodiments of the present invention, the crude ethanol product produced by the reactor, before any subsequent processing, such as purification and separation, will typically comprise unreacted acetic acid, ethanol and water. Exemplary compositional ranges for the crude ethanol product are provided in Table 1. The "others" identified in Table 1 may include, for example, esters, ethers, aldehydes, ketones, alkanes, and carbon dioxide.

TABLE 1

| CRUDE ETHANOL PRODUCT COMPOSITIONS | | | | |
|---|---|---|---|---|
| Component | Conc. (wt. %) | Conc. (wt. %) | Conc. (wt. %) | Conc. (wt. %) |
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 50 | 5 to 45 | 10 to 40 | 10 to 35 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., less than 15 wt. %, less than 10 wt. % or less than 5 wt. %. In terms of ranges, the acetic acid concentration of Table 1 may range from 0.1 wt. % to 20 wt. %, e.g., 0.2 wt. % to 15 wt. %, from 0.5 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

Ethanol Separation

Figure 2:
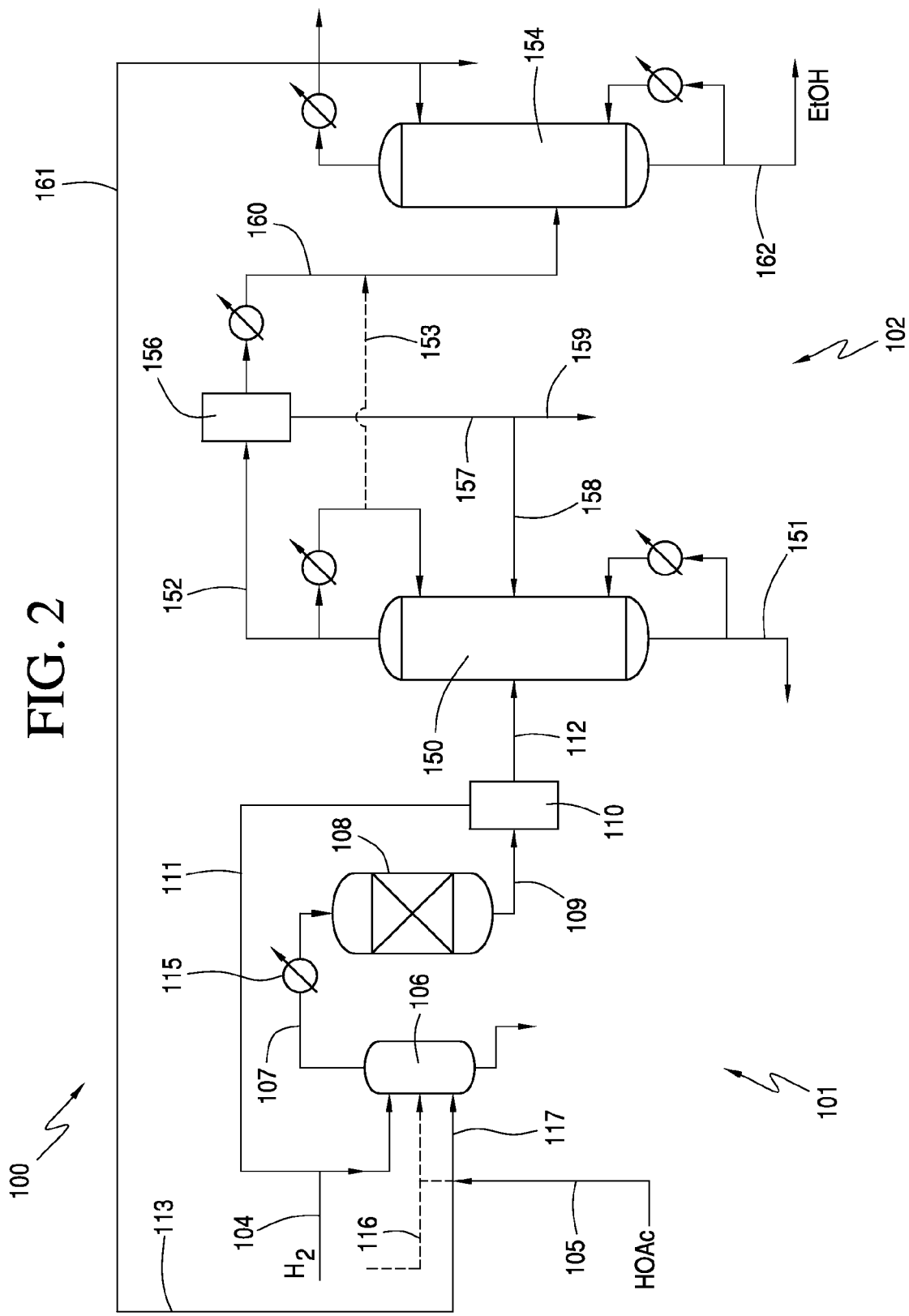
FIG. 2 is a schematic diagram of another hydrogenation process in accordance with an embodiment of the present invention.
Figure 3:
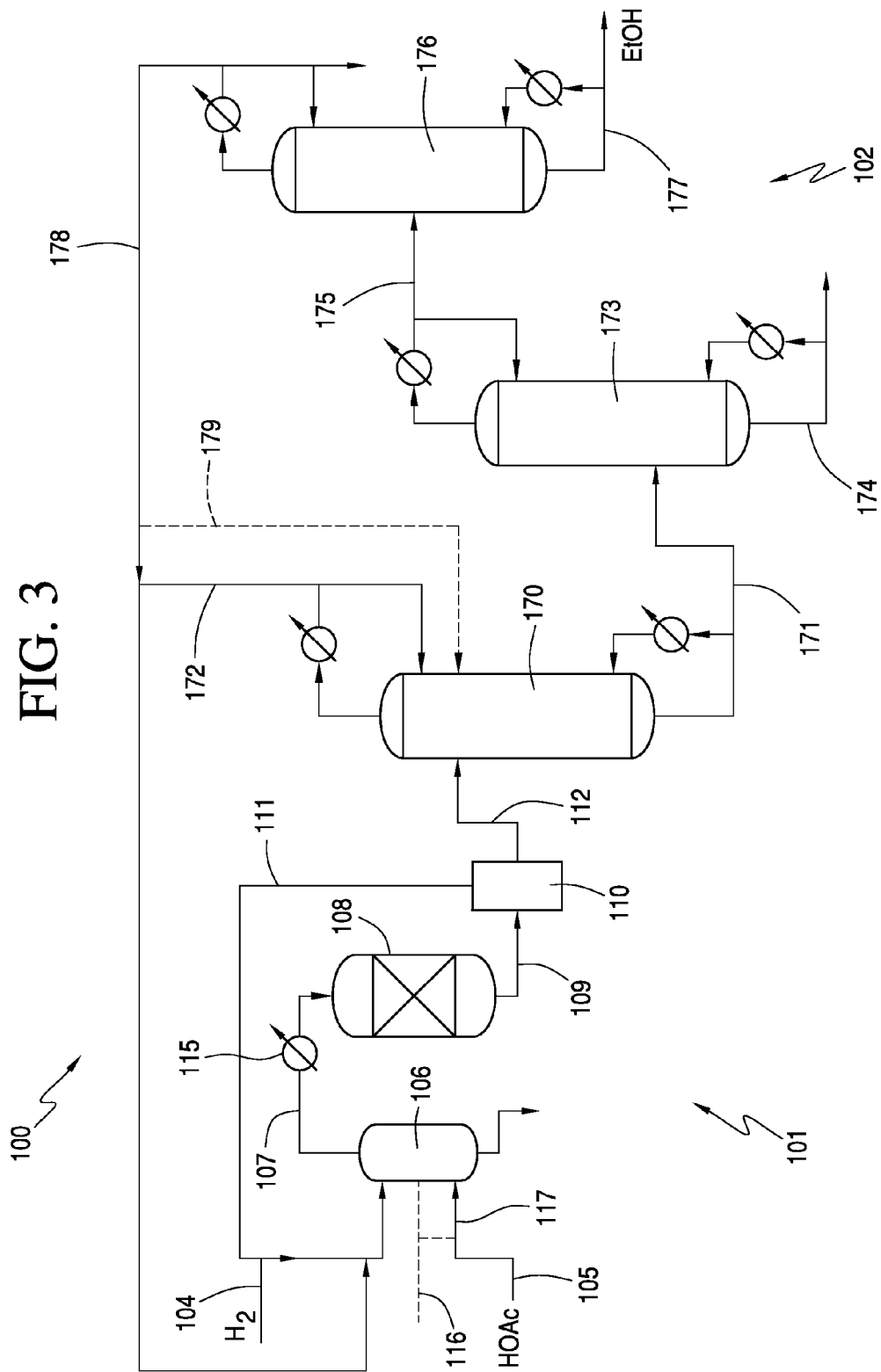
FIG. 3 is a schematic diagram of yet another hydrogenation process in accordance with an embodiment of the present invention.

Ethanol produced by the reactor may be recovered using several different techniques. In FIG. 1, the separation of the crude ethanol product uses four columns. In FIG. 2, the crude ethanol product is separated in two columns with an intervening water separation. In FIG. 3, the separation of the crude ethanol product uses two columns. Other separation systems may also be used with embodiments of the present invention.

Hydrogenation system 100 includes a reaction zone 101 and separation zone 102. Fresh acetic acid in line 105 and a liquid recycle stream from separation zone 102, shown by line 113 in FIG. 1 are mixed prior to vaporizer 106 to form a mixed feed in line 117. As stated herein, liquid recycle stream in line 113 comprises ethyl acetate. Preferably, the liquid recycle stream is a distillate stream from separation zone 102. Depending on the water concentration of fresh acetic acid in line 105 and liquid recycle stream, an optional water stream in line 116 may be fed directly to the vaporizer or may be combined with mixed feed in line 117. Hydrogen in line 104 and mixed feed in line 117 are fed to vaporizer 106 to create a vapor feed stream in line 107 that is directed to reactor 108. Hydrogen feed line 104 may be preheated to a temperature from 30° C. to 150° C., e.g., from 50° C. to 125° C. or from 60° C. to 115° C. Hydrogen feed line 104 may be fed at a pressure similar to the reactor pressure, such as from 10 kPa to 3000 kPa, e.g., from 50 kPa to 2300 kPa, or 100 kPa to 2100 kPa. In one embodiment, lines 104 and 114 may be combined and jointly fed to the vaporizer 106.

Vaporizer 106 may operate at a temperature from 20° C. to 300° C. and at a pressure from 10 kPa to 3000 kPa. Vaporizer 106 produces vapor feed stream in line 107 by transferring the acetic acid, ethyl acetate, and water from the liquid to gas phase below the boiling point of acetic acid in reactor 108 at the operating pressure of the reactor. In one embodiment, the acetic acid in the liquid state is maintained at a temperature below 160° C., e.g., below 150° C. or below 130° C. Vaporizer 106 may be operated at a temperature of at least 118° C.

The temperature of feed stream in line 107 is preferably from 100° C. to 350° C., e.g., from 120° C. to 310° C. or from 150° C. to 300° C. A preheater 115 may be used to further heat the feed stream in line 107 to the reactor temperature.

Any feed that is not vaporized is removed from vaporizer 106 in a blowdown stream and may be recycled or discarded thereto. The mass ratio of feed stream in line 107 to blowdown stream may be from 6:1 to 500:1, e.g., from 10:1 to 500:1, from 20:1 to 500:1 or from 50:1 to 500:1.

Although line 107 is shown as being directed to the top of reactor 108, line 107 may be directed to the side, upper portion, or bottom of reactor 108. Reactor 108 contains the catalyst that is used in the hydrogenation of the carboxylic acid, preferably acetic acid. In one embodiment, one or more guard beds (not shown) may be used upstream of the reactor, optionally upstream of the vaporizer 106, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product is withdrawn, preferably continuously, from reactor 108 via line 109.

The crude ethanol product in line 109 may be condensed and fed to a separator 110, which, in turn, provides a vapor stream 111 and a liquid stream 112. In some embodiments, separator 110 may comprise a flasher or a knockout pot. The separator 110 may operate at a temperature from 20° C. to 350° C., e.g., from 30° C. to 325° C. or from 60° C. to 250° C. The pressure of separator 110 may be from 100 kPa to 3000 kPa, e.g., from 125 kPa to 2500 kPa or from 150 kPa to 2200 kPa. Optionally, the crude ethanol product in line 109 may pass through one or more membranes to separate hydrogen and/or other non-condensable gases.

The vapor stream 111 exiting separator 110 may comprise hydrogen and hydrocarbons, and may be purged and/or returned to reaction zone 101. When returned to reaction zone 101, vapor stream 110 is combined with the hydrogen feed 104 and co-fed to vaporizer 106. In some embodiments, the returned vapor stream 111 may be compressed before being combined with hydrogen feed 104 or optional feed 114.

In FIG. 1, the liquid stream 112 from separator 110 is withdrawn and pumped to the side of first column 120, also referred to as an "acid separation column." In one embodiment, the contents of liquid stream 112 are substantially similar to the crude ethanol product obtained from the reactor, except that the composition has been depleted of hydrogen, carbon dioxide, methane and/or ethane, which are removed by separator 110. Accordingly, liquid stream 112 may also be referred to as a crude ethanol product. Exemplary components of liquid stream 112 are provided in Table 2. It should be understood that liquid stream 112 may contain other components, not listed in Table 2.

TABLE 2

COLUMN FEED COMPOSITION
(Liquid Stream 112)

|  | Conc. (wt. %) | Conc. (wt. %) | Conc. (wt. %) |
|---|---|---|---|
| Ethanol | 5 to 72 | 10 to 70 | 15 to 65 |
| Acetic Acid | <90 | 0 to 50 | 0 to 35 |
| Water | 5 to 50 | 5 to 45 | 10 to 40 |
| Ethyl Acetate | <30 | 1 to 25 | 3 to 20 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The lower amounts indicated as less than (<) in the tables throughout present specification are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol, 2-butanol or mixtures thereof. In one embodiment, the liquid stream 112 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, crude ethanol product in line 109 or in liquid stream 112 may be further fed to an esterification reactor, hydrogenolysis reactor, or combination thereof. An esterification reactor may be used to consume residual acetic acid present in the crude ethanol product to further reduce the amount of acetic acid that would otherwise need to be removed. Hydrogenolysis may be used to convert ethyl acetate in the crude ethanol product to ethanol.

In first column 120, unreacted acetic acid, a portion of the water, and other heavy components, if present, are removed from the composition in line 121 and are withdrawn, preferably continuously, as residue. Some or all of the residue may be returned and/or recycled back to reaction zone 101 via line 121. Recycling the acetic acid in line 121 to the vaporizer 106 may reduce the amount of heavies that need to be purged from vaporizer 106. Optionally, at least a portion of residue in line 121 may be purged from the system. Reducing the amount of heavies to be purged may improve efficiencies of the process while reducing byproducts.

First column 120 also forms an overhead distillate, which is withdrawn in line 122, and which may be condensed and refluxed, for example, at a ratio from 10:1 to 1:10, e.g., from 3:1 to 1:3 or from 1:2 to 2:1.

When column 120 is operated under standard atmospheric pressure, the temperature of the residue exiting in line 121 preferably is from 95° C. to 120° C., e.g., from 110° C. to 117° C. or from 111° C. to 115° C. The temperature of the distillate exiting in line 122 preferably is from 70° C. to 110° C., e.g., from 75° C. to 95° C. or from 80° C. to 90° C. Column 120 preferably operates at ambient pressure. In other embodiments, the pressure of first column 120 may range from 0.1 kPa to 510 kPa, e.g., from 1 kPa to 475 kPa or from 1 kPa to 375 kPa.

Exemplary components of the distillate and residue compositions for first column 120 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

ACID COLUMN 120 (FIG. 1)

|  | Conc. (wt. %) | Conc. (wt. %) | Conc. (wt. %) |
|---|---|---|---|
| Distillate |  |  |  |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column 120, the acetal appears to decompose in the column such that less or even no detectable amounts are present in the distillate and/or residue.

The distillate in line 122 preferably comprises ethanol, ethyl acetate, and water, along with other impurities, which may be difficult to separate due to the formation of binary and tertiary azeotropes. To further separate distillate, line 122 is introduced to the second column 123, also referred to as the "light ends column," preferably in the middle part of column 123, e.g., middle half or middle third. Preferably the second column 123 is an extractive distillation column, and an extraction agent is added thereto via lines 124 and/or 125.

Extractive distillation is a method of separating close boiling components, such as azeotropes, by distilling the feed in the presence of an extraction agent. The extraction agent preferably has a boiling point that is higher than the compounds being separated in the feed. In preferred embodiments, the extraction agent is comprised primarily of water. As indicated above, the first distillate in line 122 that is fed to the second column 123 comprises ethyl acetate, ethanol, and water. These compounds tend to form binary and ternary azeotropes, which decrease separation efficiency.

The molar ratio of the water in the extraction agent to the ethanol in the feed to the second column is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column distillate.

In one embodiment, an additional extraction agent, such as water from an external source, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane and chlorinated paraffins, may be added to second column 123. Some suitable extraction agents include those described in U.S. Pat. Nos. 4,379,028, 4,569,726, 5,993,610 and 6,375,807, the entire contents and disclosure of which are hereby incorporated by reference. The additional extraction agent may be combined with the recycled third residue in line 124 and co-fed to the second column 123. The additional extraction agent may also be added separately to the second column 123. In one aspect, the extraction agent comprises an extraction agent, e.g., water, derived from an external source via line 125 and none of the extraction agent is derived from the third residue.

Second column 123 may be a tray or packed column. In one embodiment, second column 123 is a tray column having from 5 to 70 trays, e.g., from 15 to 50 trays or from 20 to 45 trays. Although the temperature and pressure of second column 123 may vary, when at atmospheric pressure the temperature of the second residue exiting in line 126 preferably is from 60° C. to 90° C., e.g., from 70° C. to 90° C. or from 80° C. to 90° C. The temperature of the second distillate exiting in line 127 from second column 123 preferably is from 50° C. to 90° C., e.g., from 60° C. to 80° C. or from 60° C. to 70° C. Column 123 may operate at atmospheric pressure. In other embodiments, the pressure of second column 123 may range from 0.1 kPa to 510 kPa, e.g., from 1 kPa to 475 kPa or from 1 kPa to 375 kPa. Exemplary components for the distillate and residue compositions for second column 123 are provided in Table 4 below. It should be understood that the distillate and residue may also contain other components, not listed, such as components in the feed.

TABLE 4

SECOND COLUMN 123 (FIG. 1)

|  | Conc. (wt. %) | Conc. (wt. %) | Conc. (wt. %) |
|---|---|---|---|
| Distillate |  |  |  |
| Ethyl Acetate | 10 to 99 | 25 to 95 | 50 to 93 |
| Acetaldehyde | <25 | 0.5 to 15 | 1 to 8 |
| Water | <25 | 0.5 to 20 | 4 to 16 |
| Ethanol | <30 | 0.001 to 15 | 0.01 to 5 |
| Acetal | <5 | 0.001 to 2 | 0.01 to 1 |
| Residue |  |  |  |
| Water | 30 to 90 | 40 to 85 | 50 to 85 |
| Ethanol | 10 to 75 | 15 to 60 | 20 to 50 |
| Ethyl Acetate | <3 | 0.001 to 2 | 0.001 to 0.5 |
| Acetic Acid | <0.5 | 0.001 to 0.3 | 0.001 to 0.2 |

In preferred embodiments, the use of an extraction agent, such as the recycling of the third residue, as discussed in detail below, promotes the separation of ethyl acetate from the residue of the second column 123. For example, the weight ratio of ethyl acetate in the second residue to second distillate preferably is less than 0.4:1, e.g., less than 0.2:1 or less than 0.1:1. In embodiments that use an extractive distillation column with water as an extraction agent as the second column 123, the weight ratio of ethyl acetate in the second residue to ethyl acetate in the second distillate approaches zero. Second residue may comprise, for example, from 30% to 99.5% of the water and from 85 to 100% of the acetic acid from line 122. The second distillate in line 127 comprises ethyl acetate and additionally comprises water, ethanol, and/or acetaldehyde. Second distillate 127 may be substantially free of acetic acid. In an optional embodiment, a portion of the second distillate in line 127' may be combined with line 132 discussed below and fed to vaporizer 106.

The weight ratio of ethanol in the second residue to second distillate preferably is at least 3:1, e.g., at least 6:1, at least 8:1, at least 10:1 or at least 15:1. All or a portion of the third residue is recycled to the second column. In one embodiment, all of the third residue may be recycled until process 100 reaches a steady state and then a portion of the third residue is recycled with the remaining portion being purged from the system 100. The composition of the second residue will tend to have lower amounts of ethanol than when the third residue is not recycled. As the third residue is recycled, the composition of the second residue, as provided in Table 4, comprises less than 30 wt. % of ethanol, e.g., less than 20 wt. % or less than 15 wt. %. The majority of the second residue preferably comprises water. Notwithstanding this effect, the extractive distillation step advantageously also reduces the amount of ethyl acetate that is sent to the third column, which is highly beneficial in ultimately forming a highly pure ethanol product.

As shown, the second residue from second column 123, which comprises ethanol and water, is fed via line 126 to third column 128, also referred to as the "product column." More preferably, the second residue in line 126 is introduced in the lower part of third column 128, e.g., lower half or lower third. Third column 128 recovers ethanol, which preferably is substantially pure with respect to organic impurities and other than the azeotropic water content, as the distillate in line 129. The distillate of third column 128 preferably is refluxed as shown in FIG. 1, for example, at a reflux ratio from 1:10 to 10:1, e.g., from 1:3 to 3:1 or from 1:2 to 2:1. In one embodiment (not shown), a first portion of the third residue in line 130 is recycled to the second column and a second portion is purged and removed from the system. In one embodiment, once the process reaches steady state, the second portion of water to be purged is substantially similar to the amount water formed in the hydrogenation of acetic acid. In one embodiment, a portion of the third residue may be used to hydrolyze any other stream, such as one or more streams comprising ethyl acetate.

Third column 128 is preferably a tray column as described above and operates at atmospheric pressure or optionally at pressures above or below atmospheric pressure. The temperature of the third distillate exiting in line 129 preferably is from 60° C. to 110° C., e.g., from 70° C. to 100° C. or from 75° C. to 95° C. The temperature of the third residue in line 130 preferably is from 70° C. to 115° C., e.g., from 80° C. to 110° C. or from 85° C. to 105° C. Exemplary components of the distillate and residue compositions for third column 128 are provided in Table 5 below. It should be understood that the distillate and residue may also contain other components, not listed, such as components in the feed.

TABLE 5

THIRD COLUMN 128 (FIG. 1)

| | Conc. (wt. %) | Conc. (wt. %) | Conc. (wt. %) |
|---|---|---|---|
| Distillate | | | |
| Ethanol | 75 to 96 | 80 to 96 | 85 to 96 |
| Water | <12 | 1 to 9 | 3 to 8 |
| Acetic Acid | <12 | 0.0001 to 0.1 | 0.005 to 0.05 |
| Ethyl Acetate | <12 | 0.0001 to 0.05 | 0.005 to 0.025 |
| Acetaldehyde | <12 | 0.0001 to 0.1 | 0.005 to 0.05 |
| Diethyl Acetal | <12 | 0.0001 to 0.05 | 0.005 to 0.025 |
| Residue | | | |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns in the system 100. Preferably at least one side stream is used to remove impurities from the third column 128. The impurities may be purged and/or retained within the system 100.

The third distillate in line 129 may be further purified to form an anhydrous ethanol product stream, i.e., "finished anhydrous ethanol," using one or more additional separation systems, such as, for example, distillation columns, adsorption units, membranes, or molecular sieves. Suitable adsorption units include pressure swing adsorption units and thermal swing adsorption unit.

Returning to second column 123, the second distillate preferably is refluxed as shown in FIG. 1, optionally at a reflux ratio of 1:10 to 10:1, e.g., from 1:5 to 5:1 or from 1:3 to 3:1. The second distillate in line 127 may be purged or recycled to the reaction zone. In one embodiment, the second distillate in line 127 is further processed in a fourth column 131, also referred to as the "acetaldehyde removal column." In fourth column 131 the second distillate is separated into a fourth distillate, which comprises acetaldehyde, in line 132 and a fourth residue, which comprises ethyl acetate, in line 133. The fourth distillate preferably is refluxed at a reflux ratio from 1:20 to 20:1, e.g., from 1:15 to 15:1 or from 1:10 to 10:1, and a portion of the fourth distillate is returned to the reaction zone 101. For example, the fourth distillate may be combined with the acetic acid feed, added to the vaporizer 106, or added directly to the reactor 108. The fourth distillate preferably is co-fed with the acetic acid in feed line 105 to vaporizer 106.

Without being bound by theory, since acetaldehyde may be hydrogenated to form ethanol, the recycling of a stream that contains acetaldehyde to the reaction zone increases the yield of ethanol and decreases byproduct and waste generation. In another embodiment, the acetaldehyde may be collected and utilized, with or without further purification, to make useful products including but not limited to n-butanol, 1,3-butanediol, and/or crotonaldehyde and derivatives.

The fourth residue of fourth column 131 may be purged via line 133. The fourth residue primarily comprises ethyl acetate and ethanol, which may be suitable for use as a solvent mixture or in the production of esters. In one preferred embodiment, the acetaldehyde is removed from the second distillate in fourth column 131 such that no detectable amount of acetaldehyde is present in the residue of column 131.

Fourth column 131 is preferably a tray column as described above and preferably operates above atmospheric pressure. In one embodiment, the pressure is from 120 kPa to 5,000 kPa, e.g., from 200 kPa to 4,500 kPa, or from 400 kPa to 3,000 kPa. In a preferred embodiment the fourth column 131 may operate at a pressure that is higher than the pressure of the other columns.

The temperature of the fourth distillate exiting in line 132 preferably is from 60° C. to 110° C., e.g., from 70° C. to 100° C. or from 75° C. to 95° C. The temperature of the residue in line 133 preferably is from 70° C. to 115° C., e.g., from 80° C. to 110° C. or from 85° C. to 110° C. Exemplary components of the distillate and residue compositions for fourth column 131 are provided in Table 6 below. It should be understood that the distillate and residue may also contain other components, not listed, such as components in the feed.

TABLE 6

FOURTH COLUMN 131 (FIG. 1)

|  | Conc. (wt. %) | Conc. (wt. %) | Conc. (wt. %) |
|---|---|---|---|
| Distillate |  |  |  |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue |  |  |  |
| Ethyl Acetate | 40 to 100 | 50 to 100 | 60 to 100 |
| Ethanol | <40 | 0.001 to 30 | 0.01 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

In one embodiment, a portion of the third residue in line 130 is recycled to second column 123. In one embodiment, recycling the third residue further reduces the aldehyde components in the second residue and concentrates these aldehyde components in second distillate in line 127 and thereby sent to the fourth column 131, wherein the aldehydes may be more easily separated. The third distillate in line 129 may have lower concentrations of aldehydes and esters due to the recycling of third residue in line 124.

FIG. 2 illustrates another exemplary separation system. The reaction zone 101 of FIG. 2 is similar to FIG. 1 and produces a liquid stream 112, e.g., crude ethanol product, for further separation. In one preferred embodiment, the reaction zone 101 of FIG. 2 operates at above 80% acetic acid conversion, e.g., above 90% conversion or above 99% conversion. Thus, the acetic acid concentration in the liquid stream 112 may be low.

Liquid stream 112 is introduced in the middle or lower portion of a first column 150, also referred to as acid-water column. For purposes of convenience, the columns in each exemplary separation process, may be referred as the first, second, third, etc., columns, but it is understood that first column 150 in FIG. 2 operates differently than the first column 120 of FIG. 1. In one embodiment, no entrainers are added to first column 150. In FIG. 2, first column 150, water and unreacted acetic acid, along with any other heavy components, if present, are removed from liquid stream 112 and are withdrawn, preferably continuously, as a first residue in line 151. Preferably, a substantial portion of the water in the crude ethanol product that is fed to first column 150 may be removed in the first residue, for example, up to about 75% or to about 90% of the water from the crude ethanol product. First column 150 also forms a first distillate, which is withdrawn in line 152.

When column 150 is operated under about 170 kPa, the temperature of the residue exiting in line 151 preferably is from 90° C. to 130° C., e.g., from 95° C. to 120° C. or from 100° C. to 115° C. The temperature of the distillate exiting in line 152 preferably is from 60° C. to 90° C., e.g., from 65° C. to 85° C. or from 70° C. to 80° C. In some embodiments, the pressure of first column 150 may range from 0.1 kPa to 510 kPa, e.g., from 1 kPa to 475 kPa or from 1 kPa to 375 kPa.

The first distillate in line 152 comprises water, in addition to ethanol and other organics. In terms of ranges, the concentration of water in the first distillate in line 152 preferably is from 4 wt. % to 38 wt. %, e.g., from 7 wt. % to 32 wt. %, or from 7 to 25 wt. %. A portion of first distillate in line 153 may be condensed and refluxed, for example, at a ratio from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 150. The condensed portion of the first distillate may also be fed to a second column 154.

The remaining portion of the first distillate in 152 is fed to a water separation unit 156. Water separation unit 156 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separator 156 is a pressure swing adsorption (PSA) unit. The PSA unit is optionally operated at a temperature from 30° C. to 160° C., e.g., from 80° C. to 140° C., and a pressure from 0.01 kPa to 550 kPa, e.g., from 1 kPa to 150 kPa. The PSA unit may comprise two to five beds. Water separator 156 may remove water in an amount necessary for the ethanol product, which may vary. For hydrous ethanol application, water separator 156 may remove water in an amount greater than 10% from the portion of first distillate in line 152, e.g., greater than 20% or greater than 35%. For anhydrous ethanol applications, water separator 156 may remove at least 95% of the water from the portion of first distillate in line 152, and more preferably from 95% to 99.99% of the water from the first distillate, in a water stream 157. All or a portion of water stream 157 may be returned to column 150 in line 158, where the water preferably is ultimately recovered from column 150 in the first residue in line 151. Additionally or alternatively, all or a portion of water stream 157 may be purged via line 159. The remaining portion of first distillate exits the water separator 156 as ethanol mixture stream 160. Ethanol mixture stream 160 may have a low concentration of water of less than 10 wt. %, e.g., less than 6 wt. % or less than 2 wt. %. Exemplary components of ethanol mixture stream 160 and first residue in line 151 are provided in Table 7 below. It should also be understood that these streams may also contain other components, not listed, such as components derived from the feed.

TABLE 7

FIRST COLUMN 150 WITH PSA (FIG. 2)

|  | Conc. (wt. %) | Conc. (wt. %) | Conc. (wt. %) |
|---|---|---|---|
| Ethanol Mixture Stream |  |  |  |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | <90 | 1 to 50 | 2 to 35 |
| Water | 30 to 100 | 45 to 95 | 60 to 90 |
| Ethanol | <1 | <0.9 | <0.3 |

Preferably, ethanol mixture stream 160 is not returned or refluxed to first column 150. The condensed portion of the first distillate in line 153 may be combined with ethanol mixture stream 160 to control the water concentration fed to the second column 154. For example, in some embodiments the first distillate may be split into equal portions, while in other embodiments, all of the first distillate may be condensed or all of the first distillate may be processed in the water separation unit. In FIG. 2, the condensed portion in line 153 and ethanol mixture stream 160 are co-fed to second column 154. In other embodiments, the condensed portion in line 153 and ethanol mixture stream 160 may be separately fed to second column 154. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 154 in FIG. 2, also referred to as the "light ends column," removes ethyl acetate and acetaldehyde from the first distillate in line 153 and/or ethanol mixture stream 160. Ethyl acetate and acetaldehyde are removed as a second distillate in line 161 and ethanol is removed as the second residue in line 162. Second column 108 may be a tray column or packed column. In one embodiment, second column 154 is a tray column having from 5 to 70 trays, e.g., from 15 to 50 trays or from 20 to 45 trays.

Second column 154 operates at a pressure ranging from 0.1 kPa to 510 kPa, e.g., from 10 kPa to 450 kPa or from 50 kPa to 350 kPa. Although the temperature of second column 154 may vary, when at about 20 kPa to 70 kPa, the temperature of the second residue exiting in line 162 preferably is from 30° C. to 75° C., e.g., from 35° C. to 70° C. or from 40° C. to 65° C. The temperature of the second distillate exiting in line 161 preferably is from 20° C. to 55° C., e.g., from 25° C. to 50° C. or from 30° C. to 45° C.

The total concentration of water fed to second column 154 preferably is less than 10 wt. %, as discussed above. When first distillate in line 153 and/or ethanol mixture stream comprises minor amounts of water, e.g., less than 1 wt. % or less than 0.5 wt. %, additional water may be fed to the second column 154 as an extractive agent in the upper portion of the column. A sufficient amount of water is preferably added via the extractive agent such that the total concentration of water fed to second column 154 is from 1 to 10 wt. % water, e.g., from 2 to 6 wt. %, based on the total weight of all components fed to second column 154. If the extractive agent comprises water, the water may be obtained from an external source or from an internal return/recycle line from one or more of the other columns or water separators.

Suitable extractive agents may also include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. When extractive agents are used, a suitable recovery system, such as a further distillation column, may be used to recycle the extractive agent.

Exemplary components for the second distillate and second residue compositions for the second column 154 are provided in Table 8, below. It should be understood that the distillate and residue may also contain other components, not listed in Table 8.

TABLE 8

SECOND COLUMN 154 (FIG. 2)

|  | Conc. (wt. %) | Conc. (wt. %) | Conc. (wt. %) |
|---|---|---|---|
| Second Distillate |  |  |  |
| Ethyl Acetate | 5 to 90 | 10 to 80 | 15 to 75 |
| Acetaldehyde | <60 | 1 to 40 | 1 to 35 |
| Ethanol | <45 | 0.001 to 40 | 0.01 to 35 |
| Water | <20 | 0.01 to 10 | 0.1 to 5 |
| Second Residue |  |  |  |
| Ethanol | 80 to 99.5 | 85 to 97 | 60 to 95 |
| Water | <20 | 0.001 to 15 | 0.01 to 10 |
| Ethyl Acetate | <1 | 0.001 to 2 | 0.001 to 0.5 |
| Acetic Acid | <0.5 | <0.01 | 0.001 to 0.01 |

The second residue in FIG. 2 comprises one or more impurities selected from the group consisting of ethyl acetate, acetic acid, acetaldehyde, and diethyl acetal. The second residue may comprise at least 100 wppm of these impurities, e.g., at least 250 wppm or at least 500 wppm. In some embodiments, the second residue may contain substantially no ethyl acetate or acetaldehyde.

The second distillate in line 161, which comprises ethyl acetate and/or acetaldehyde, preferably is refluxed as shown in FIG. 2, for example, at a reflux ratio from 1:30 to 30:1, e.g., from 1:10 to 10:1 or from 1:3 to 3:1. In one aspect, not shown, the second distillate 161 or a portion thereof may be returned to reactor 108. The ethyl acetate and/or acetaldehyde in the second distillate may be further reacted in hydrogenation reactor 108.

In one embodiment, the second distillate in line 161 and/or a refined second distillate, or a portion of either or both streams, may be further separated to produce an acetaldehyde-containing stream and an ethyl acetate-containing stream. This may allow a portion of either the resulting acetaldehyde-containing stream or ethyl acetate-containing stream to be recycled to reactor 108 while purging the other stream. The purge stream may be valuable as a source of either ethyl acetate and/or acetaldehyde.

FIG. 3 illustrates another exemplary separation system. The reaction zone 101 of FIG. 3 is similar to FIG. 1 and produces a liquid stream 112, e.g., crude ethanol product, for further separation. In one preferred embodiment, the reaction zone 101 of FIG. 3 operates at above 80% acetic acid conversion, e.g., above 90% conversion or above 99% conversion. Thus, the acetic acid concentration in the liquid stream 112 may be low.

In the exemplary embodiment shown in FIG. 3, liquid stream 112 is introduced in the upper part of first column 170, e.g., upper half or upper third. In addition to liquid stream 112, an optional extractive agent (not shown) and an optional ethyl acetate recycle stream in line 179 may also be fed to first column 170. The optional extractive agent may comprise water that is introduced above the feed location of the liquid stream 112. In some embodiment, the optional extractive agent may be a dilute acid stream comprising up to 20 wt. % acetic acid. Also, the optional ethyl acetate recycle stream may have a relatively high ethanol concentration, e.g. from 70 to 90 wt. %, and may be fed above or near the feed point of the liquid stream 112.

In one embodiment, first column 170 is a tray column having from 5 to 90 theoretical trays, e.g. from 10 to 60 theoretical trays or from 15 to 50 theoretical trays. The number of actual trays for each column may vary depending on the tray efficiency, which is typically from 0.5 to 0.7 depending on the type of tray. The trays may be sieve trays, fixed valve trays, movable valve trays, or any other suitable design known in the art. In other embodiments, a packed column having structured packing or random packing may be employed.

When first column 170 is operated under 50 kPa, the temperature of the residue exiting in line 171 preferably is from 20° C. to 100° C., e.g., from 30° C. to 90° C. or from 40° C. to 80° C. The base of column 170 may be maintained at a relatively low temperature by withdrawing a residue stream comprising ethanol, ethyl acetate, water, and acetic acid, thereby providing an energy efficiency advantage. The temperature of the distillate exiting in line 172 preferably at 50 kPa is from 10° C. to 80° C., e.g., from 20° C. to 70° C. or from 30° C. to 60° C. The pressure of first column 170 may range from 0.1 kPa to 510 kPa, e.g., from 1 kPa to 475 kPa or from 1 kPa to 375 kPa. In some embodiments, first column 170 may operate under a vacuum of less than 70 kPa, e.g., less than 50 kPa, or less than 20 kPa. Operating under a vacuum may decrease the reboiler duty and reflux ratio of first column 170. However, a decrease in operating pressure for first column 170 does not substantially affect column diameter.

In first column 170, a weight majority of the ethanol, water, acetic acid, are removed from an organic feed, which comprises liquid stream 112 and the optional ethyl acetate recycle stream in line 179, and are withdrawn, preferably continuously, as residue in line 171. This includes any water added as the optional extractive agent. Concentrating the ethanol in the residue reduces the amount of ethanol that is recycled to reactor 108 and in turn reduces the size of reactor 108. Preferably less than 10% of the ethanol from the organic feed, e.g., less than 5% or less than 1% of the ethanol, is returned to reactor 108 from first column 170. In addition, concentrating the ethanol also will concentrate the water and/or acetic acid in the residue. In one embodiment, at least 90% of the ethanol from the organic feed is withdrawn in the residue, and more preferably at least 95%. In addition, ethyl acetate may also be present in the first residue in line 171. The reboiler duty may decrease with an ethyl acetate concentration increase in the first residue in line 171.

First column 170 also forms a distillate, which is withdrawn in line 172, and which may be condensed and refluxed, for example, at a ratio from 30:1 to 1:30, e.g., from 10:1 to 1:10 or from 5:1 to 1:5. Higher mass flow ratios of water to organic feed may allow first column 170 to operate with a reduced reflux ratio.

First distillate in line 172 preferably comprises a weight majority of the acetaldehyde and ethyl acetate from liquid stream 112, as well as from the optional ethyl acetate recycle stream in line 179. In one embodiment, the first distillate in line 172 comprises a concentration of ethyl acetate that is less than the ethyl acetate concentration for the azeotrope of ethyl acetate and water, and more preferably less than 75 wt. %.

In some embodiments, first distillate in stream 172 also comprises ethanol. Returning the first distillate comprising ethanol to the reactor may require an increase in reactor capacity to maintain the same level of ethanol efficiency. In one embodiment, it is preferred to return to the reactor less than 10% of the ethanol from the crude ethanol stream, e.g., less than 5% or less than 1%. In terms of ranges, the amount of returned ethanol is from 0.01 to 10% of the ethanol in the crude ethanol stream, e.g. from 0.1 to 5% or from 0.2 to 1%. In one embodiment, to reduce the amount of ethanol returned, the ethanol may be recovered from the first distillate in line 172 using an optional extractor or extractive distillation column.

Exemplary components of the distillate and residue compositions for first column 170 are provided in Table 3 below.

It should also be understood that the distillate and residue may also contain other components, not listed in Table 3. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 9

FIRST COLUMN 170 (FIG. 3)

|  | Conc. (wt. %) | Conc. (wt. %) | Conc. (wt. %) |
|---|---|---|---|
| Distillate |  |  |  |
| Ethyl Acetate | 10 to 85 | 15 to 80 | 20 to 75 |
| Acetaldehyde | 0.1 to 70 | 0.2 to 65 | 0.5 to 65 |
| Acetal | <0.1 | <0.1 | <0.05 |
| Acetone | <0.05 | 0.001 to 0.03 | 0.01 to 0.025 |
| Ethanol | 3 to 55 | 4 to 50 | 5 to 45 |
| Water | 0.1 to 20 | 1 to 15 | 2 to 10 |
| Acetic Acid | <2 | <0.1 | <0.05 |
| Residue |  |  |  |
| Acetic Acid | 0.1 to 50 | 0.5 to 40 | 1 to 30 |
| Water | 5 to 40 | 5 to 35 | 10 to 25 |
| Ethanol | 10 to 75 | 15 to 70 | 20 to 65 |
| Ethyl Acetate | 0.005 to 30 | 0.03 to 25 | 0.08 to 1 |

In one embodiment of the present invention, first column 170 may be operated at a temperature where most of the water, ethanol, and acetic acid are removed into the residue stream and only a small amount of ethanol and water is collected in the distillate stream due to the formation of binary and tertiary azeotropes. The weight ratio of water in the residue in line 171 to water in the distillate in line 172 may be greater than 1:1, e.g., greater than 2:1. There may be more water in residue in line 171 when an optional extractive agent is used. The weight ratio of ethanol in the residue to ethanol in the distillate may be greater than 1:1, e.g., greater than 2:1.

The amount of acetic acid in the first residue may vary depending primarily on the conversion in reactor 108. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The distillate preferably is substantially free of acetic acid, e.g., comprising less than 1000 ppm, less than 500 ppm or less than 100 ppm acetic acid. The distillate may be purged from the system or recycled in whole or part to reactor 108. In some embodiments, the distillate may be further separated, e.g., in a distillation column (not shown), into an acetaldehyde stream and an ethyl acetate stream. Either of these streams may be returned to reactor 108 or separated from system 100 as additional products. The ethyl acetate stream may also be hydrolyzed or reduced with hydrogen, via hydrogenolysis, to produce ethanol. When additional ethanol is produced, it is preferred that the additional ethanol is recovered and not directed to reactor 108.

Some species, such as acetals, may decompose in first column 170 such that very low amounts, or even no detectable amounts, of acetals remain in the distillate or residue.

To recover ethanol, first residue in line 171 may be further separated depending on the concentration of acetic acid and/or ethyl acetate.

In FIG. 3, residue in line 171 is further separated in a second column 173, also referred to as an "acid column." Second column 173 yields a second residue in line 174 comprising acetic acid and water, and a second distillate in line 175 comprising ethanol and ethyl acetate. In one embodiment, a weight majority of the water and/or acetic acid fed to second column 173 is removed in the second residue in line 174, e.g., at least 60% of the water and/or acetic acid is removed in the second residue in line 174 or more preferably at least 80% of the water and/or acetic acid. An acid column may be desirable, for example, when the acetic acid concentration in the first residue is greater 50 wppm, e.g., greater than 0.1 wt. %, greater than 1 wt. %, e.g., greater than 5 wt. %.

In one embodiment, a portion of the first residue in line 171 may be preheated prior to being introduced into second column 173, as shown in FIG. 3. After preheating first residue in line 171 may be converted into a partial vapor feed having less than 30 mol. % of the contents in the vapor phase, e.g., less than 25 mol. % or less than 20 mol. %. In terms of ranges, from 1 to 30 mol. % is in the vapor phase, e.g., from 5 to 20 mol. %. Greater vapor phase contents result in increased energy consumption and a significant increase in the size of second column 173.

Second column 173 operates in a manner to concentrate the ethanol from first residue so that a majority of the ethanol is carried overhead. Thus, the residue of second column 173 may have a low ethanol concentration of less than 5 wt. %, e.g. less than 1 wt. % or less than 0.5 wt. %. Lower ethanol concentrations may be achieved without significant increases in reboiler duty or column size. Thus, in some embodiments, it is efficient to reduce the ethanol concentration in the residue to less than 50 wppm, or more preferably less than 25 wppm. As described herein, the residue of second column 173 may be treated and lower concentrations of ethanol allow the residue to be treated without generating further impurities.

In FIG. 3, the first residue in line 171 is introduced to second column 173 preferably in the top part of column 173, e.g., top half or top third. Feeding first residue in line 171 in a lower portion of second column 173 may unnecessarily increase the energy requirements. Acid column 173 may be a tray column or packed column. In FIG. 3, second column 173 may be a tray column having from 10 to 110 theoretical trays, e.g. from 15 to 95 theoretical trays or from 20 to 75 theoretical trays. Additional trays may be used if necessary to further reduce the ethanol concentration in the residue. In one embodiment, the reboiler duty and column size may be reduced by increasing the number of trays.

Although the temperature and pressure of second column 173 may vary, when at atmospheric pressure the temperature of the second residue in line 174 preferably is from 95° C. to 160° C., e.g., from 100° C. to 150° C. or from 110° C. to 145° C. In one embodiment, first residue in line 171 is preheated to a temperature that is within 20° C. of the temperature of second residue in line 174, e.g., within 15° C. or within 10° C. The temperature of the second distillate exiting in line 175 from second column 173 preferably is from 50° C. to 120° C., e.g., from 75° C. to 118° C. or from 80° C. to 115° C. The temperature gradient may be sharper in the base of second column 173.

The pressure of second column 173 may range from 0.1 kPa to 510 kPa, e.g., from 1 kPa to 475 kPa or from 1 kPa to 375 kPa. In one embodiment, second column 173 operates above atmospheric pressure, e.g., above 170 kPa or above 375 kPa. Second column 173 may be constructed of a material such as 316L SS, Allot 2205 or Hastelloy C, depending on the operating pressure. The reboiler duty and column size for second column 173 remain relatively constant until the ethanol concentration in the second distillate in line 175 is greater than 90 wt. %.

Second column 173 also forms an overhead, which is withdrawn, and which may be condensed and refluxed, for example, at a ratio from 12:1 to 1:12, e.g., from 10:1 to 1:10 or from 8:1 to 1:8. The overhead preferably comprises 85 to 92 wt. % ethanol, e.g., about 87 to 90 wt. % ethanol, with the remaining balance being water and ethyl acetate. In one embodiment, water may be removed prior to recovering the ethanol product as described above in FIG. 2. In one embodiment, the overhead, prior to water removal, may comprise less than 15 wt. % water, e.g., less than 10 wt. % water or less than 8 wt. % water. Overhead vapor may be fed to water separator, which may be an adsorption unit, membrane, molecular sieves, extractive column distillation, or a combination thereof.

Exemplary components for the distillate and residue compositions for second column 173 are provided in Table 10 below. It should be understood that the distillate and residue may also contain other components, not listed in Table 10. For example, in optional embodiments, when ethyl acetate is in the feed to reactor 108, second residue in line 174 exemplified in Table 10 may also comprise high boiling point components.

TABLE 10

SECOND COLUMN 173 (FIG. 3)

|  | Conc. (wt. %) | Conc. (wt. %) | Conc. (wt. %) |
| --- | --- | --- | --- |
| Second Distillate | | | |
| Ethanol | 80 to 96 | 85 to 92 | 87 to 90 |
| Ethyl Acetate | <30 | 0.001 to 15 | 0.005 to 4 |
| Acetaldehyde | <20 | 0.001 to 15 | 0.005 to 4 |
| Water | <20 | 0.001 to 10 | 0.01 to 8 |
| Acetal | <2 | 0.001 to 1 | 0.005 to 0.5 |
| Second Residue | | | |
| Acetic Acid | 0.1 to 55 | 0.2 to 40 | 0.5 to 35 |
| Water | 45 to 99.9 | 55 to 99.8 | 65 to 99.5 |
| Ethyl Acetate | <0.1 | 0.0001 to 0.05 | 0.0001 to 0.01 |
| Ethanol | <5 | 0.002 to 1 | 0.005 to 0.5 |

The weight ratio of ethanol in second distillate in line 175 to ethanol in the second residue in line 174 preferably is at least 35:1. Preferably, second distillate in line 175 is substantially free of acetic acid and may contain, if any, trace amounts of acetic acid.

In one embodiment, ethyl acetate fed to second column 173 may concentrate in the second distillate in line 175. Thus, preferably no ethyl acetate is withdrawn in the second residue in line 174. Advantageously this allows most of the ethyl acetate to be subsequently recovered without having to further process the second residue in line 174.

In one embodiment, as shown in FIG. 3, due to the presence of ethyl acetate in second distillate in line 175, an additional third column 176 may be used. Third column 176, referred to as a "product" column, is used for removing ethyl acetate from second distillate in line 175 and producing an ethanol product in the third residue in line 177. Product column 176 may be a tray column or packed column. In FIG. 3, third column 176 may be a tray column having from 5 to 90 theoretical trays, e.g. from 10 to 60 theoretical trays or from 15 to 50 theoretical trays.

The feed location of second distillate in line 175 may vary depending on ethyl acetate concentration and it is preferred to feed second distillate in line 175 to the upper portion of third column 176. Higher concentrations of ethyl acetate may be fed at a higher location in third column 176. The feed location should avoid the very top trays, near the reflux, to avoid excess reboiler duty requirements for the column and an increase in column size. For example, in a column having 45 actual trays, the feed location should between 10 to 15 trays from the top. Feeding at a point above this may increase the reboiler duty and size of third column 176.

Second distillate in line 175 may be fed to third column 176 at a temperature of up to 70° C., e.g., up to 50° C., or up to 40° C. In some embodiments it is not necessary to further preheat second distillate in line 175.

Ethyl acetate may be concentrated in the third distillate in line 178. Due to the relatively lower amounts of ethyl acetate fed to third column 176, third distillate in line 178 also comprises substantial amounts of ethanol. To recover the ethanol, third distillate in line 178 may be fed to first column 170 as an optional ethyl acetate recycle stream 179. Depending on the ethyl acetate concentration of optional ethyl acetate recycle stream 179 this stream may be introduced above or near the feed point of the liquid stream 112. Depending on the targeted ethyl acetate concentration in the distillate of first column 172 the feed point of optional ethyl acetate recycle stream 179 will vary. Liquid stream 112 and optional ethyl acetate recycle stream 179 collectively comprise the organic feed to first column 170. In one embodiment, organic feed comprises from 1 to 25% of optional ethyl acetate recycle stream 179, e.g., from 3% to 20% or from 5% to 15%. This amount may vary depending on the production of reactor 108 and amount of ethyl acetate to be recycled.

Because optional ethyl acetate recycle stream 179 increases the demands on the first and second columns, it is preferred that the ethanol concentration in third distillate in line 179 be from 70 to 90 wt. %, e.g., from 72 to 88 wt. %, or from 75 to 85 wt. %. In other embodiments, a portion of third distillate in line 178 may be purged from the system as additional products, such as an ethyl acetate solvent. In addition, ethanol may be recovered from a portion of the third distillate in line 178 using an extractant, such as benzene, propylene glycol, and cyclohexane, so that the raffinate comprises less ethanol to recycle.

In an optional embodiment, the third residue may be further processed to recover ethanol with a desired amount of water, for example, using a further distillation column, adsorption unit, membrane or combination thereof, may be used to further remove water from third residue in line 177 as necessary.

Third column 176 is preferably a tray column as described above and preferably operates at atmospheric pressure. The temperature of the third residue in line 177 exiting from third column 176 preferably is from 65° C. to 110° C., e.g., from 70° C. to 100° C. or from 75° C. to 80° C. The temperature of the third distillate in line 178 exiting from third column 176 preferably is from 30° C. to 70° C., e.g., from 40° C. to 65° C. or from 50° C. to 65° C.

The pressure of third column 176 may range from 0.1 kPa to 510 kPa, e.g., from 1 kPa to 475 kPa or from 1 kPa to 375 kPa. In some embodiments, third column 176 may operate under a vacuum of less than 70 kPa, e.g., less than 50 kPa, or less than 20 kPa. Decreases in operating pressure substantially decreases column diameter and reboiler duty for third column 176.

Exemplary components for ethanol mixture stream and residue compositions for third column 176 are provided in Table 11 below. It should be understood that the distillate and residue may also contain other components, not listed in Table 11.

TABLE 11

| PRODUCT COLUMN (FIG. 3) | | | |
|---|---|---|---|
| | Conc. (wt. %) | Conc. (wt. %) | Conc. (wt. %) |
| Third Distillate | | | |
| Ethanol | 70 to 99 | 72 to 95 | 75 to 90 |
| Ethyl Acetate | 1 to 30 | 1 to 25 | 1 to 15 |
| Acetaldehyde | <15 | 0.001 to 10 | 0.1 to 5 |
| Water | <10 | 0.001 to 2 | 0.01 to 1 |
| Acetal | <2 | 0.001 to 1 | 0.01 to 0.5 |
| Third Residue | | | |
| Ethanol | 80 to 99.5 | 85 to 97 | 90 to 95 |
| Water | <3 | 0.001 to 2 | 0.01 to 1 |
| Ethyl Acetate | <1.5 | 0.0001 to 1 | 0.001 to 0.5 |
| Acetic Acid | <0.5 | <0.01 | 0.0001 to 0.01 |

Some of the residues withdrawn from the separation zone 102 comprise acetic acid and water. Depending on the amount of water and acetic acid contained in the residue of first column, e.g., 120 in FIG. 1, 150 in FIG. 2, or residue of second column 173 in FIG. 3, the residue may be treated in one or more of the following processes. The following are exemplary processes for further treating the residue and it should be understood that any of the following may be used regardless of acetic acid concentration. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from the residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to the reactor 108. The resulting water stream may be used as an extractive agent or to hydrolyze an ester-containing stream in a hydrolysis unit.

In other embodiments, for example, where the residue comprises less than 50 wt. % acetic acid, possible options include one or more of: (i) returning a portion of the residue to reactor 108, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added.

Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. %, the residue may be disposed of to a waste water treatment facility without further processing. The organic content, e.g., acetic acid content, of the residue beneficially may be suitable to feed microorganisms used in a waste water treatment facility.

The columns shown in FIGS. 1 to 3 may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The ethanol product produced by the process of the present invention may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 12.

TABLE 12

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 12, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst, such as zeolite catalysts or phosphotungstic acid catalysts, can be employed to dehydrate ethanol, as described in copending U.S. Pub. Nos. 2010/0030002 and 2010/0030001 and WO2010146332, the entire contents and disclosures of which are hereby incorporated by reference.

In order that the invention disclosed herein may be more efficiently understood, an example is provided below. It should be understood that these examples are for illustrative purposes only and is not to be construed as limiting the invention in any manner.

EXAMPLES

Examples 1 to 3 were prepared to show three different feed streams may be fed to vaporizer 106. The acetic acid, ethyl acetate, acetaldehyde and diethyl acetal amounts were kept constant. The amount of water and ethanol was varied.

TABLE 13

| Component | Example 1 Wt. % | Example 2 Wt. % | Example 3 Wt. % |
|---|---|---|---|
| Acetic acid | 62 | 62 | 62 |
| Ethyl acetate | 20 | 20 | 20 |
| Ethanol | 15 | 8 | 1 |
| Water | 1 | 8 | 15 |
| Acetaldehyde | 1 | 1 | 1 |
| Diethyl acetal | 1 | 1 | 1 |

Each of the feed streams in Examples 1 to 3 were vaporized and fed to reactor 108. The acetic acid concentration and ethyl acetate conversion are reported in Table 14.

TABLE 14

| | 1500 $hr^{-1}$ | | 2200 $hr^{-1}$ | |
|---|---|---|---|---|
| | Acetic Acid Conversion (%) | Ethyl Acetate Conversion (%) | Acetic Acid Conversion (%) | Ethyl Acetate Conversion (%) |
| Example 1 | 96.5 | 10.7 | 94.5 | −7.2 |
| Example 2 | 96.3 | 21.7 | 93.5 | −2.2 |
| Example 3 | 95.7 | 29.3 | 93 | 3.1 |

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising:
   hydrogenating a feed stream in a reactor in the presence of a catalyst to form a crude ethanol product, wherein the catalyst is substantially free of copper and zinc, and oxides thereof; and
   separating at least a portion of the crude ethanol product in two or more columns to produce ethanol and a liquid recycle stream comprising ethyl acetate;
   wherein the feed stream is produced by vaporizing an acetic acid stream, the liquid recycle stream and a water stream in a vaporizer; and
   wherein the total amount of water fed to the vaporizer is at least 0.01 wt. %.

2. The process of claim 1, wherein the acetic acid stream comprises the water stream.

3. The process of claim 1, wherein the liquid recycle stream comprises the water stream.

4. The process of claim 1, wherein the total amount of water fed to the vaporizer is at least 0.1 wt. % water.

5. The process of claim 1, wherein the total amount of water fed to the vaporizer is from 0.01 wt. % to 20 wt. % water.

6. The process of claim 1, wherein the liquid recycle stream comprises ethyl acetate, ethanol, water and/or acetaldehyde or mixtures thereof.

7. The process of claim 1, wherein a volumetric ratio of acetic acid stream to liquid recycle stream is at least 1.5:1.

8. The process of claim 1, wherein a volumetric ratio of acetic acid stream to liquid recycle stream is from 1.5:1 to 20:1.

9. The process of claim 1, wherein conversion of ethyl acetate is at least 1%.

10. The process of claim 1, wherein the catalyst comprises a first metal selected from the group consisting of iron, cobalt, nickel, ruthenium, rhodium, palladium, osmium, iridium, platinum, titanium, chromium, rhenium, molybdenum, and tungsten, and a second metal is selected from the group consisting of molybdenum, tin, chromium, iron, cobalt, vanadium, tungsten, palladium, platinum, lanthanum, cerium, manganese, ruthenium, rhenium, gold, and nickel, wherein the second metal is different than the first metal.

11. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

12. A process for producing ethanol, comprising:
   hydrogenating a feed stream in a reactor in the presence of a catalyst to form a crude ethanol product, wherein the catalyst is substantially free of copper and zinc, and oxides thereof;
   separating at least a portion of the crude ethanol product in a first distillation column to yield a first residue comprising acetic acid and a first distillate comprising ethanol, ethyl acetate, and water;
   removing water from at least a portion of the first distillate to yield an ethanol mixture stream comprising less than 10 wt. % water; and
   separating a portion of the ethanol mixture stream in a second distillation column to yield a second residue comprising ethanol and a second distillate comprising ethyl acetate;
   wherein the feed stream is produced by vaporizing an acetic acid stream, the second distillate and a water stream in a vaporizer; and
   wherein the total amount of water fed to the vaporizer is at least 0.01 wt. %.

13. A process for producing ethanol, comprising:
   hydrogenating a feed stream in a reactor in the presence of a catalyst to form a crude ethanol product, wherein the catalyst is substantially free of copper and zinc, and oxides thereof;
   separating a portion of the crude ethanol product in a first distillation column to yield a first distillate comprising ethyl acetate and acetaldehyde, and a first residue comprising ethanol, acetic acid, water, or mixtures thereof;
   separating a portion of the first residue in a second distillation column to yield a second residue comprising acetic acid and water and a second distillate comprising ethanol and ethyl acetate; and
   separating a portion of the second distillate in a third distillation column to yield a third residue comprising ethanol and a third distillate comprising ethyl acetate;
   wherein the feed stream is produced by vaporizing an acetic acid stream, the third distillate and a water stream in a vaporizer; and wherein the total amount of water fed to the vaporizer is at least 0.01 wt. % water.

14. The process of claim 13, wherein the total amount of water fed to the vaporizer is from 0.01 wt. % to 20 wt. % water.

15. The process of claim 13, wherein an extractive agent is fed to the first column.

16. A process for producing ethanol, comprising:
hydrogenating a feed stream in a reactor in the presence of a catalyst to form a crude ethanol product, wherein the catalyst is substantially free of copper and zinc, and oxides thereof; and
separating at least a portion of the crude ethanol product in two or more columns to produce ethanol and a liquid recycle stream;
wherein the feed stream is produced by vaporizing an acetic acid stream, the liquid recycle stream and a water stream; and
wherein more water is fed to the vaporizer than ethanol on a molar basis.

17. The process of claim 16, wherein a volumetric ratio of acetic acid stream to liquid recycle stream is at least 1.5:1.

\* \* \* \* \*